(12) United States Patent
Rezach et al.

(10) Patent No.: US 8,870,881 B2
(45) Date of Patent: Oct. 28, 2014

(54) SPINAL CORRECTION SYSTEM AND METHOD

(75) Inventors: William Alan Rezach, Atoka, TN (US); Charles Anthony Dickinson, Bartlett, TN (US); Rodney Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 197 days.

(21) Appl. No.: 13/441,095

(22) Filed: Apr. 6, 2012

(65) Prior Publication Data

US 2013/0268011 A1    Oct. 10, 2013

(51) Int. Cl.
  *A61B 17/70*    (2006.01)

(52) U.S. Cl.
  USPC .......................................... 606/86 A; 606/99

(58) Field of Classification Search
  USPC ........... 606/246–278, 300–321, 86 A, 96, 99, 606/104
  See application file for complete search history.

(56) References Cited

U.S. PATENT DOCUMENTS

| | | | |
|---|---|---|---|
| 7,481,828 B2 | 1/2009 | Mazda et al. | |
| 7,959,654 B2 | 6/2011 | Mazda et al. | |
| 2009/0138048 A1* | 5/2009 | Baccelli et al. | 606/263 |
| 2009/0248077 A1* | 10/2009 | Johns | 606/246 |
| 2009/0326585 A1 | 12/2009 | Baccelli et al. | |
| 2010/0249845 A1 | 9/2010 | Meunier | |
| 2011/0034956 A1 | 2/2011 | Mazda et al. | |
| 2011/0112581 A1 | 5/2011 | Clement | |
| 2011/0184469 A1* | 7/2011 | Ballard et al. | 606/279 |

* cited by examiner

*Primary Examiner* — Mary Hoffman
*Assistant Examiner* — Christina Negrellirodrigue

(57) ABSTRACT

A surgical instrument comprises a first member having a first surface defining a first cavity for disposal of a first implant. A distal end is configured to mate with a recess of a connector and defines a second cavity. A second member is configured for movable disposal in the second cavity. A third member is connected to the proximal end of the second member and the first implant. The second member is axially movable in a first direction to tension the first implant and in a second direction to release tension from the first implant. Methods of use are disclosed.

19 Claims, 13 Drawing Sheets

US 8,870,881 B2

SPINAL CORRECTION SYSTEM AND METHOD

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, for stabilization of a treated section of a spine. This disclosure describes an improvement over these prior art technologies.

SUMMARY

Accordingly, a spinal correction system is provided. In one embodiment, in accordance with the principles of the present disclosure, the system comprises a surgical instrument. The instrument includes a first member having a first surface defining a first cavity for disposal of a first implant. A distal end is configured to mate with a recess of a connector and defines a second cavity. A second member is configured for movable disposal in the second cavity. A third member is connected to the proximal end of the second member and the first implant. The second member is axially movable in a first direction to tension the first implant and in a second direction to release tension from the first implant.

In one embodiment, the spinal implant system comprises a connector. The connector includes an outer surface that defines a recess, a first passageway and a second passageway disposed in a transverse orientation relative to the first passageway. The system includes a tether that is disposable in at least the first passageway and extends between a proximal end and a distal end. The tether comprises a plurality of spaced apart lateral openings disposed longitudinally therealong. The distal end of the tether includes a loop configured for disposal about vertebrae. The system includes a spinal rod that is disposable in at least the second passageway and extends between a first end and a second end. An instrument defines a longitudinal axis and includes a body that extends between a proximal end and a distal end. The body includes an outer surface having a concave portion that defines an axial channel configured for disposal of the tether. The outer surface of the body defines a lateral opening disposed in communication with the axial channel. The distal end of the body includes an angled surface and a reduced diameter portion configured to mate with the recess. The body further includes an inner threaded surface that defines a translation cavity. The instrument further includes a lead screw that includes a threaded outer surface that is engageable with the inner threaded surface. The instrument further includes a handle fixed with the lead screw via a pinned interface such that the lead screw is relatively rotatable therefrom. The handle includes a lateral projection configured for disposal in the lateral openings. The handle defines a lateral opening disposed in communication with the axial channel such that the lead screw is rotatable in a clockwise direction to cause axial translation of the body relative to the lead screw in a first direction such that the projection tensions the tether and the lead screw is rotatable in a counter clockwise direction to cause axial translation of the body relative to the lead screw in a second direction to release tension from the tether.

In one embodiment, a method for treating a spine disorder is provided. The method comprises the steps of: providing a first flexible implant; disposing the first flexible implant with a first vertebra; providing a first connector including an outer surface defining a recess and an inner surface defining a first passageway and a second passageway; disposing the first flexible implant in the first passageway; providing a second implant; disposing the second implant in the second passageway; providing an instrument comprising a first member having a first surface defining a first cavity and a distal end, the first member defining a second cavity, a second member configured for movable disposal in the second cavity and a third member connected to the proximal end of the second member; disposing the first flexible implant in the first cavity; mating the distal end with the recess; delivering the connector to adjacent the first vertebra with the instrument; connecting the first flexible implant with the third member; and axially translating the first member relative to the second member in a first direction such that the third member tensions the first flexible implant and in a second direction such that the third member releases tension from the first flexible implant.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
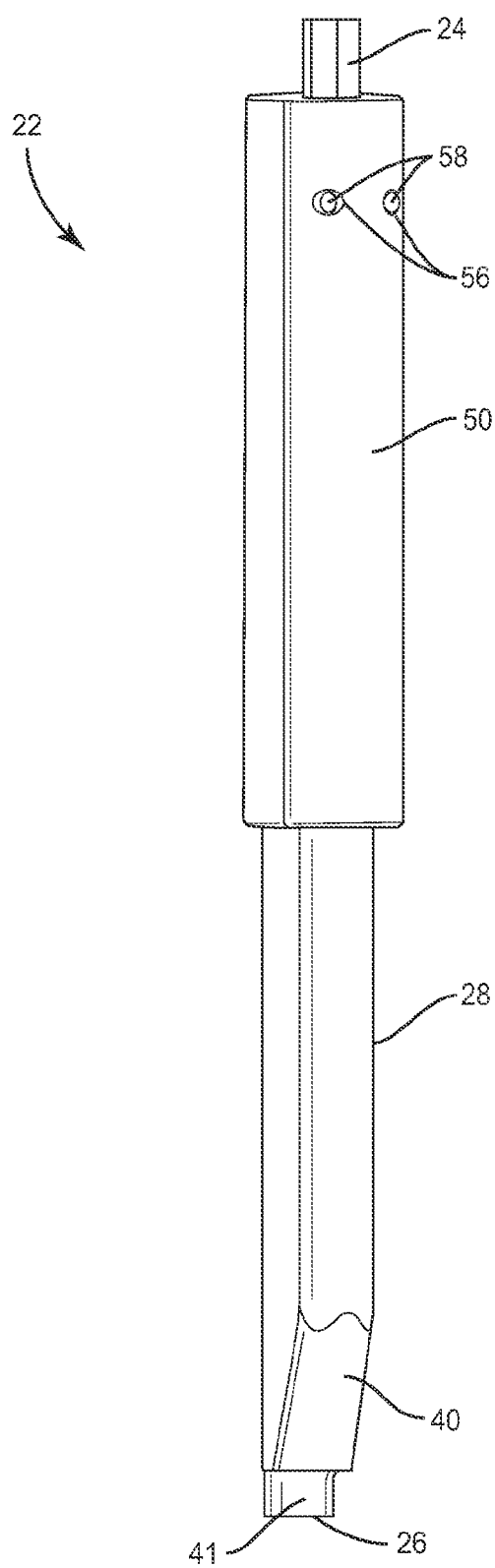
FIG. 1 is a perspective view of one particular embodiment of components of a spinal correction system in accordance with the principles of the present disclosure.
Figure 2:
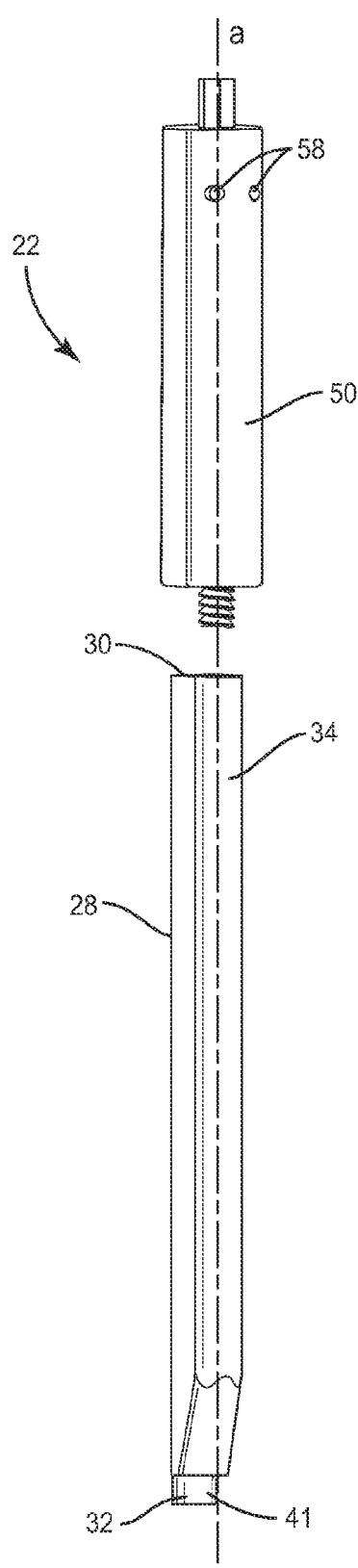
FIG. 2 is a perspective view of the components of the system shown in FIG. 1 with parts separated.

The exemplary embodiments of a surgical system and related methods of use are discussed in terms of medical devices for the treatment of musculoskeletal disorders and more particularly, in terms of a spinal correction system. It is envisioned that the spinal correction system may be employed in applications for correction of deformities, such as scoliosis and kyphosis.

In one embodiment, the spinal correction system includes a connector. The connector includes a setscrew having a tip that forces a spinal rod laterally. The connector includes a hole for disposal of a tether. In one embodiment, the hole has a threaded diameter that increases grip strength with a tether. In one embodiment, the tether can be cylindrical having a diameter. In one embodiment, the tether can have a flat configuration having a thickness and allowing ease of passing the tether about a transverse process and/or lamina of vertebrae.

In one embodiment, the spinal correction system is employed with a procedure for placing multiple tethers. The multiple tethers are placed one at a time with each vertebral level. Each tether has a loop on one end. After placing the tether under lamina/transverse process of a vertebral level, the tether is placed through a loop for attachment to the vertebral level, similar to a lasso or stringer attachment configuration. The connector is mounted onto the rod and provisionally locked to maintain the connector from sliding, spinning and/or disengaging from the rod. The tethers are then passed through the connector.

In one embodiment, the spinal correction system includes a surgical instrument. The surgical instrument attaches to the tether from the side, preventing the tether from having to pass through the instrument. The instrument and the connector are configured for engagement such that the connector docks onto or into the instrument. The instrument applies tension to the tether, creating a tight fixation between the tether and the selected vertebrae. In one embodiment, the instrument is sized to allow implant placement at each vertebral level, for example, for segmental reduction.

In one embodiment, the surgical instrument includes a tether anchor. The tether anchor secures placement of the tether when it is drawn through the side of the instrument. The instrument includes a pattern of slots positioned approximately 10 millimeters (mm) apart where an angled post is inserted to tension the tether. In one embodiment, the instrument is spring loaded, which allows the instrument to be placed in an open and closed position.

In one embodiment, the instrument is open from the side, therefore allowing ease of tether placement. The tether has slots that mate with a tilted and/or angled blunt pin. In one embodiment, the pin is sharp to pierce through and lock a tether into position. In one embodiment, a set screw or a lead screw is locked to a handle and rotates about its axis. Rotation is accomplished via a pinned interface. It is contemplated that rotation may occur through various types of interfaces, such as, for example, retaining rings. The set screw or lead screw is a left hand thread that engages an instrument base. As the lead screw or set screw is rotated clockwise, it loosens or lengthens the instrument thereby tensioning the tether. As the instrument is turned counter-clockwise, it tightens or decreases instrument length thereby removing tension on the tether. The base of the instrument is angled on one side to maintain clearance for setscrew tightening and or placement. In one embodiment, the instrument includes a loop that wraps around the setscrew to help stabilize placement if the instrument has a tendency to lean or tilt. In one embodiment, such tensioning of the tether can deliver a connector along the tether and/or draw vertebrae to a spinal rod. In one embodiment, the surgical instrument includes a loop that wraps around a setscrew to stabilize placement of the instrument and avoid leaning and/or tilting of the instrument.

It is contemplated that one or all of the components of the spinal correction system may be disposable, peel-pack, pre-packed sterile devices. One or all of the components of the system may be reusable. The system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a spinal correction system in accordance with the principles of the present disclosure. Alternate embodiments are also disclosed. Reference will now be made in detail to the exemplary embodiments of the present disclosure, which are illustrated in the accompanying figures. Turning now to FIGS. 1-9, there is illustrated components of a system, such as, for example, a spinal correction system 20 in accordance with the principles of the present disclosure.

The components of spinal correction system 20 can be fabricated from biologically acceptable materials suitable for medical applications, including metals, synthetic polymers, ceramics, bone material, tissue and/or their composites, depending on the particular application and/or preference of a medical practitioner. For example, the components of spinal correction system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKEL-ITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 20 may have material composites, including the above materials, to achieve various desired characteristics such as strength, rigidity, elasticity, compliance, biomechanical performance, durability and radiolucency or imaging preference. The components of system 20, individually or collectively, may also be fabricated from a heterogeneous material such as a combination of two or more of the above-described materials. The components of system 20 may be monolithically formed, integrally connected or include fastening elements and/or instruments, as described herein.

System 20 is employed, for example, with an open, mini-open or minimally invasive including percutaneous surgical technique to attach a longitudinal element to a spine that has a spinal disorder. In one embodiment, the longitudinal element may be affixed to a selected section of the spine and/or other anatomy while allowing for growth and adjustments to a concave side of a plurality of vertebrae for a correction treatment to treat various spine pathologies, such as, for example, adolescent idiopathic scoliosis and Scheuermann's kyphosis.

Spinal correction system 20 includes an implant instrument 22. Instrument 22 extends between a proximal end 24 and a distal end 26. Instrument 22 defines a longitudinal axis a that extends between ends 24, 26. Instrument 22 has a non-uniform cross-section configuration. It is contemplated that the cross-section of instrument 22 may have various configurations, for example, cylindrical, round, oval, rectangular, polygonal, irregular, tapered, offset, staggered and uniform. It is further envisioned that one or all of the surfaces of instrument 22 may have alternate surface configurations, such as, for example, rough, threaded for connection with surgical instruments, arcuate, undulating, porous, semi-porous, dimpled, polished and/or textured according to the requirements of a particular application.

Instrument 22 includes a first member, such as, for example, body 28. Body 28 extends between a proximal end 30 and a distal end 32. Body 28 has a rectangular cross-sectional configuration. It is contemplated that body 28 may have various configurations, for example, cylindrical, round, oval, rectangular, polygonal, irregular, tapered, offset, staggered and uniform. Body 28 includes an outer surface 34. Outer surface 34 has a smooth surface configuration. It is envisioned that outer surface 34 may have alternate surface configurations, such as, for example, rough, threaded for connection with surgical instruments, arcuate, undulating, porous, semi-porous, dimpled, polished and/or textured according to the requirements of a particular application.

Outer surface 34 includes a concave surface that extends from end 30 to end 32. The concave surface defines an axial channel 36. Channel 36 is configured for engagement with a spinal implant, such as, for example, a tether, as described herein. A lateral opening 38 is disposed in communication with channel 36 and extends between ends 30, 32. Channel 36 and opening 38 facilitate loading of the tether with instrument 22 and attachment thereto. End 32 is configured for engagement with a connector, as described herein, to dock a connecter passageway with instrument 22.

End 32 includes an angled surface 40. Surface 40 is configured to facilitate clearance about a setscrew, discussed herein, of a connector to engage with instrument 22, as described herein. It is contemplated that portion 40 may be variously configured according to the requirements of a particular application. End 32 includes a reduced dimension portion, such as, for example, a tip 41. Tip 41 is configured to mate and/or dock with a connector, as described.

Figure 8:
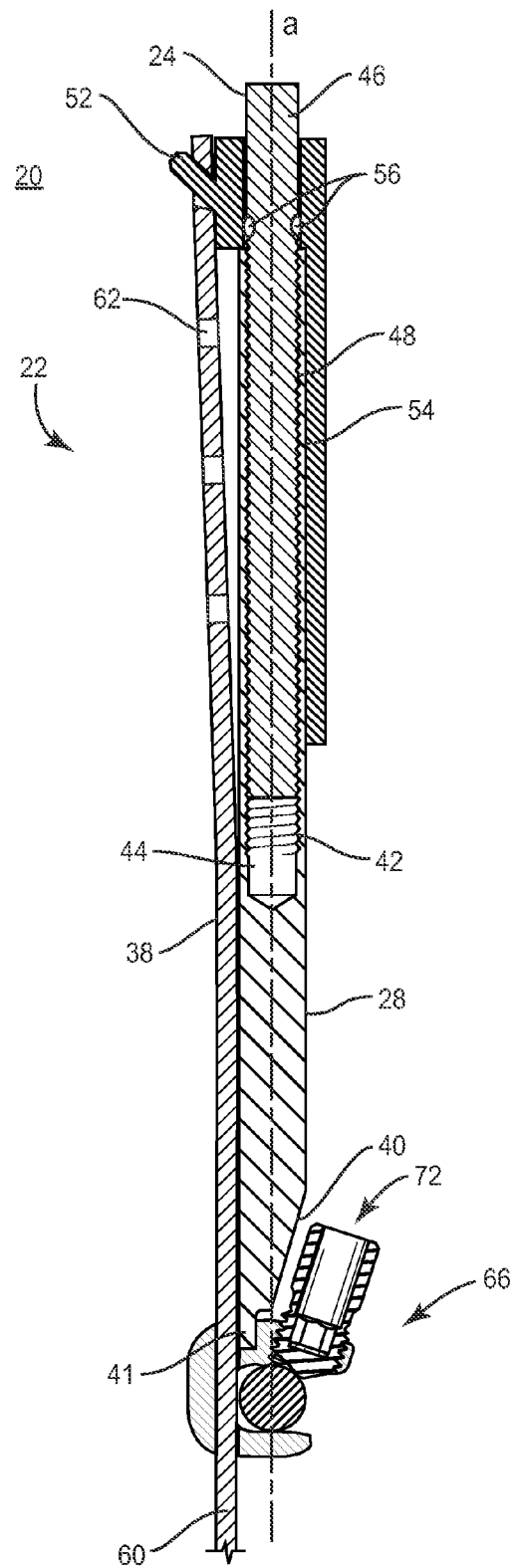
FIG. 8 is a cross-section view of the system shown in FIG. 7.

Body 28 includes an inner threaded surface 42, as shown in FIG. 8. Surface 42 defines a translation cavity 44 that extends through at least a portion of body 28. Cavity 44 extends along longitudinal axis a. Cavity 44 is configured for engagement and axial translation with a screw, such as, for example, a lead screw described herein.

Instrument 22 includes a second member, such as, for example, lead screw 46 that extends between a proximal end 47 and a distal end 49. Screw 46 includes a threaded outer surface 48 that extends from the proximal end to the distal end of the screw. Surface 48 is configured for rotational engagement with cavity 44. Screw 46 has a cylindrical cross-section configuration. It is contemplated that screw 46 may have various configurations, for example, round, oval, rectangular, polygonal, irregular, tapered, offset, staggered, uniform and non-uniform. Screw 46 is configured for axial translation relative to body 28. In one embodiment, surface 48 includes a left hand thread such that upon rotation in a first direction, such as, for example, a clockwise direction, screw 46 loosens from body 28 to tension the tether and upon rotation in a second direction, such as, for example, a counter clockwise direction, screw 46 tightens with body 28 to release tension from the tether.

A third member, such as, for example, handle 50 extends between a proximal end 51 and a distal end 53. Handle 50 has a rectangular cross section configuration. It is contemplated that handle 50 may have various configurations similar to those alternatives described herein. Handle 50 includes a lateral angled projection, such as, for example, pin 52. It is envisioned that pin 52 can be variously configured with regard to size and shape, and the shape may be, for example, rectangular, triangular, polygonal, and hexagonal. Pin 52 has a blunt tip. Pin 52 is configured for engagement with a plurality of spaced apart lateral openings of a tether, as described herein. In one embodiment, pin 52 is sharp or pointed to pierce through a tether. Screw 46 is locked to handle 50 via a pinned interface, discussed herein, which facilitates rotation of screw 46 about axis a.

Figure 3:
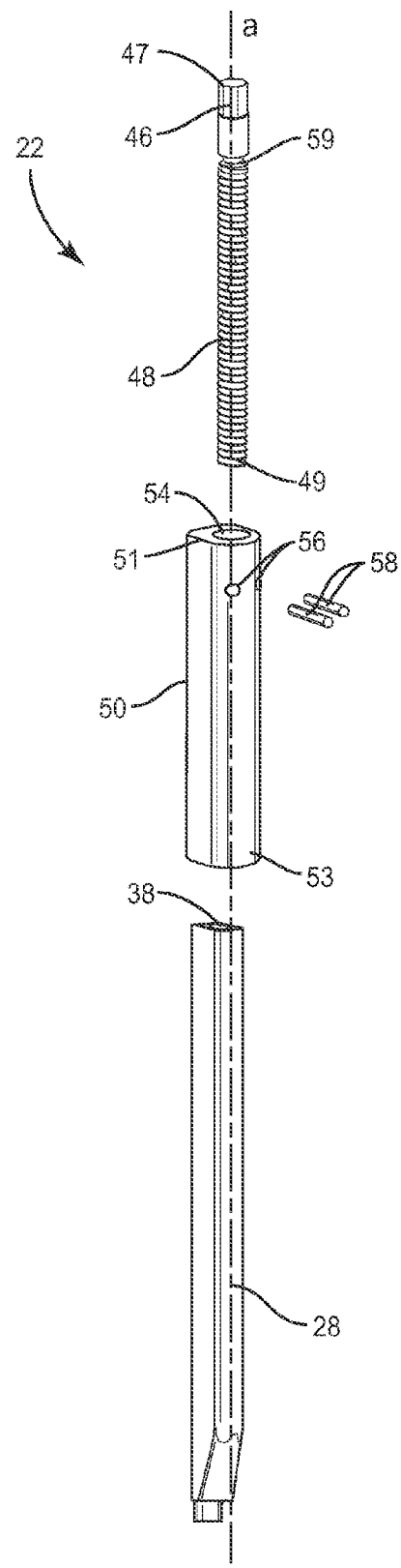
FIG. 3 is a perspective view of the components of the system shown in FIG. 1 with parts separated.

Handle 50 includes an opening 54 that extends through handle 50 along longitudinal axis a. Opening 54 has a cylindrical cross section configuration. It is contemplated that opening 54 may have alternative configurations, such as, for example, those described herein. Handle 50 is configured for engagement with screw 46 and body 28. For example, screw 46 is disposable within opening 54 and the distal end of handle 50 is fixed with end 30 of body 28. Handle 50 includes slots 56 located at the proximal end of handle 50. Slots 56 are configured for engagement with pins 58. The pinned interface includes pins 58 and a circumferential cavity 59 of screw 46, as shown in FIG. 3. Cavity 59 is configured for disposal of pins 58 and slidably engageable therewith to facilitate free rotation of screw 46 relative to body 28. Pins 58 are fixed with slots 56 and support screw 46 with body 28 for rotation relative thereto.

In one embodiment, instrument 22 includes a loop. The loop is configured for engagement with a connector and wraps around a set screw to increase placement stabilization during implantation. The loop may be fabricated from materials described herein.

Spinal correction system 20 includes a first implant, such as, for example, a tether 60. Tether 60 is a flexible longitudinal element that extends between a first end and a second free end. The first end includes a loop defining a cavity. The cavity is configured for disposal of a portion of tether 60 such that tether 60 can be tensioned about a targeted portion of an anatomy of a body for attachment of tether 60 with the targeted portion of the anatomy, as will be described. It is contemplated that tether 60 may be manipulated manually and/or with a surgical tensioning instrument, such as, for example, instrument 22. It is further contemplated that the targeted portion of the anatomy may include a lamina, transverse process and/or pedicle regions of a vertebral level. It is envisioned that spinal correction system 20 may include one or a plurality of tethers 60, each tether being configured for disposal about a single and separate vertebral level. It is further envisioned that a single vertebral level may include one or a plurality of tethers 60.

Tether 60 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of tether 60 includes movement in a lateral or side to side direction and prevents expanding and/or extension in an axial direction upon tensioning of the first end and attachment with a targeted portion of the anatomy. It is envisioned that all or only a portion of tether 60 may have a semi-rigid, rigid or elastic configuration, and/or have elastic properties such that tether 60 provides a selective amount of expansion and/or extension in an axial direction. It is further envisioned that tether 60 may be compressible in an axial direction. Tether 60 can include a plurality of separately attachable or connectable portions or sections, such as bands or loops, or may be monolithically formed as a single continuous element.

Tether 60 includes a plurality of spaced apart lateral openings 62 configured for engagement with pin 52 of handle 50. Tether 60 can have a uniform thickness/diameter. It is envisioned that tether 60 may have various surface configurations, such as, for example, smooth and/or surface configurations to enhance fixation, such as, for example, rough, arcuate, undulating, porous, semi-porous, dimpled, polished and/or textured according to the requirements of a particular application. It is contemplated that the thickness defined by tether 60 may be uniformly increasing or decreasing, or have alternate diameter dimensions along its length. It is further contemplated that tether 60 may have various cross section configurations, such as, for example, oval, oblong, triangular, rectangular, square, polygonal, irregular, uniform, non-uniform, variable and/or tapered. It is contemplated that the surface of tether 60 may include engaging structures, such as, for example, barbs, raised elements and/or spikes to facilitate engagement with tissue of the targeted anatomy.

It is contemplated that tether 60 may have various lengths, according to the requirements of a particular application. It is further contemplated that tether 60 may be braided, such as a rope, or include a plurality of elongated elements to provide a predetermined force resistance. It is envisioned that tether 60 may be made from autograft and/or allograft, and be configured for resorbable or degradable applications. In one embodiment, tether 60 is a cadaver tendon. In one embodiment, tether 60 is a tendon that may be harvested, for example, from a patient or donor. It is contemplated that a tendon harvested from a patient may be affixed in remote locations with the patient's body.

Spinal correction system 20 includes a second implant, such as, for example, a spinal rod 64 having a cylindrical cross section configuration. Spinal rod 64 defines a central axis and includes an arcuate outer surface. Spinal rod 64 extends between a first end and a second end. It is envisioned that spinal correction system 20 may include one or a plurality of spinal rods 64, which may be relatively disposed in a side by side, irregular, uniform, non-uniform, offset and/or staggered orientation or arrangement.

It is contemplated that spinal rod 64 can have a uniform thickness/diameter. It is envisioned that spinal rod 64 may have various surface configurations, such as, for example, rough, threaded for connection with surgical instruments, arcuate, undulating, dimpled, polished and/or textured according to the requirements of a particular application. It is contemplated that the thickness defined by spinal rod 64 may be uniformly increasing or decreasing, or have alternate diameter dimensions along its length. It is further contemplated that spinal rod 64 may have various cross section configurations, such as, for example, oval, oblong, triangular, rectangular, square, polygonal, irregular, uniform, non-uniform, variable and/or tapered. It is contemplated that spinal rod 64 may have various lengths, according to the requirements of a particular application.

Spinal correction system 20 includes an implant connector, such as, for example, a connector 66. Connector 66 includes a body having an angled configuration. The body includes an outer surface. It is contemplated that spinal correction system 20 may include one or a plurality of implant connectors spaced apart and disposed along spinal rod 64, as will be described, which may be relatively disposed in a side by side, irregular, uniform, non-uniform, offset and/or staggered orientation or arrangement, along one or a plurality of spinal rods.

The body of connector 66 includes a recess 65 configured for disposal and support of tip 41. Tip 41 engages recess 65 to dock instrument 22 with connector 66. Tip 41 is releasably engaged with recess 65 in a tight fitting engagement. The body of connector 66 includes a first inner surface 67 that defines a first cavity, such as, for example, a first passageway 68. First passageway 68 is substantially cylindrical and extends through the body. Inner surface 67 includes a gripping element, such as, for example, an internal thread form configured to enhance fixation with tether 60, according to the requirements of a particular application. It is contemplated that the thread form may include a single thread turn or a plurality of discrete threads. It is further contemplated that other gripping elements may be located on the inner surface 67, such as, for example, a nail configuration, barbs, expanding elements, raised elements and/or spikes to facilitate engagement of the first inner surface with tether 60. It is envisioned that inner surface 67 may include one or a plurality of gripping elements.

First passageway 68 defines a first axis and is configured for disposal of tether 60. First passageway 68 facilitates movement of tether 60 therealong and fixation with the first inner surface upon tensioning of tether 60, according to the requirements of a particular application, for fixation with a targeted portion of the anatomy.

It is envisioned that all or only a portion of first passageway 68 may have alternate cross section configurations, such as, for example, oval, oblong, triangular, square, polygonal, irregular, uniform, non-uniform, offset, staggered, undulating, arcuate, variable and/or tapered. It is contemplated that first passageway 68 may include one or a plurality of openings that may extend through the body to the outer surface. It is contemplated that all or only a portion of the first inner surface may have alternate surface configurations to enhance fixation with tether 60, including or alternative to a gripping element, such as, for example, rough, arcuate, undulating, mesh, porous, semi-porous, dimpled and/or textured according to the requirements of a particular application.

The body of connector 66 includes a second inner surface 69 that defines a second cavity, such as, for example, a second passageway 70. Second passageway 70 is substantially cylindrical and extends through the body to a third interior cavity, as will be discussed. Inner surface 69 includes an internal thread form configured for engagement with a coupling member, as will be discussed. It is contemplated that the thread form may include a single thread turn or a plurality of discrete threads.

It is envisioned that all or only a portion of second passageway 70 may have alternate cross section configurations, such as, for example, oval, oblong, triangular, square, polygonal, irregular, uniform, non-uniform, offset, staggered, undulating, arcuate, variable and/or tapered. It is contemplated that second passageway 70 may include one or a plurality of openings that may extend through the body to the outer surface.

Second passageway 70 defines a second axis disposed at an angular orientation. It is envisioned that all or only a portion of the axis corresponding to second passageway 70 may be disposed at alternate orientations, relative to the first axis corresponding to first passageway 68, such as, for example, transverse, perpendicular and/or other angular orientations such as acute or obtuse and/or may be offset or staggered.

Second passageway 70 is configured for disposal of a coupling member, such as, for example, a set screw 72. Set screw 72 defines a central axis, which is disposed in a co-axial alignment with the second axis upon disposal of set screw 72 with second passageway 70. Set screw 72 has a tubular body that includes an outer surface and an inner surface.

The body of connector 66 includes a third inner surface 73 that defines a third cavity, such as, for example, a third passageway 74. Third passageway 74 has an oblong configuration and extends through the body. It is envisioned that all or only a portion of third passageway 74 may have alternate cross section configurations, such as, for example, oval, cylindrical, triangular, square, polygonal, irregular, uniform, non-uniform, offset, staggered, undulating, arcuate, variable and/or tapered. It is contemplated that third passageway 74 may include one or a plurality of openings that may extend through the body to the outer surface.

Third passageway 74 defines a third axis disposed in a transverse orientation relative to the first and second axes of connector 66. It is envisioned that all or only a portion of the third axis may be disposed at alternate orientations, relative to the first axis and/or the second axis, such as, for example, transverse, perpendicular and/or other angular orientations such as acute or obtuse and/or may be offset or staggered. Third passageway 74 is configured for disposal of spinal rod 64 such that connector 66 can be mounted with spinal rod 64, according to the requirements of a particular application.

Figure 4:
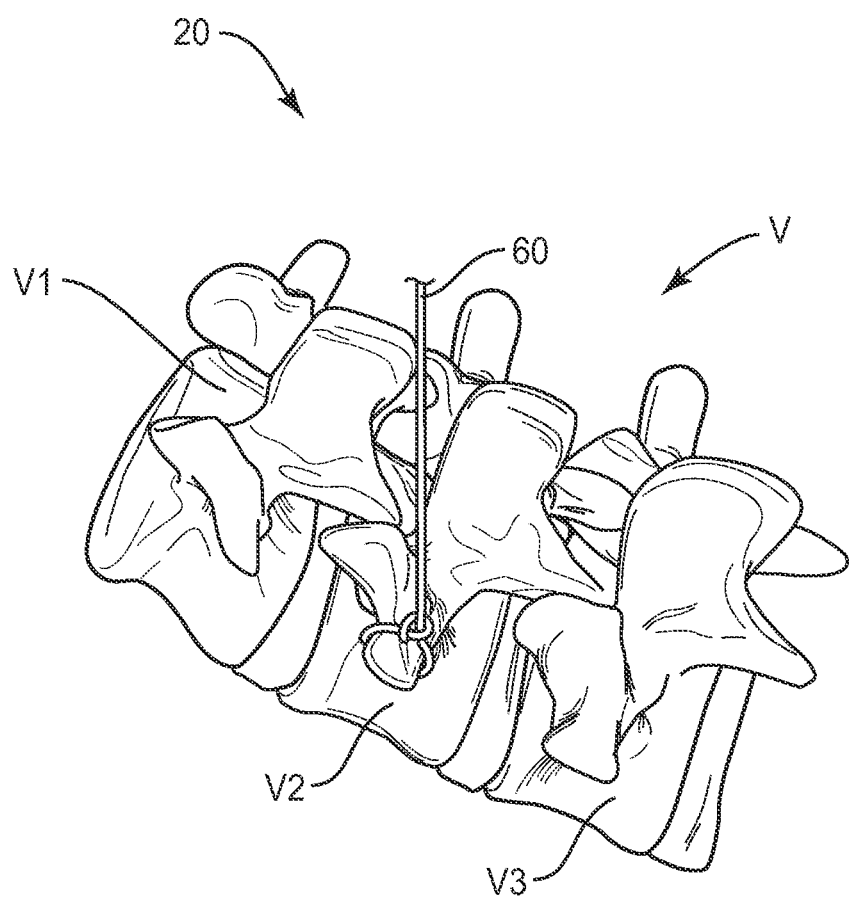
FIG. 4 is a perspective view of a component of the system shown in FIG. 1 disposed with vertebrae.
Figure 5:
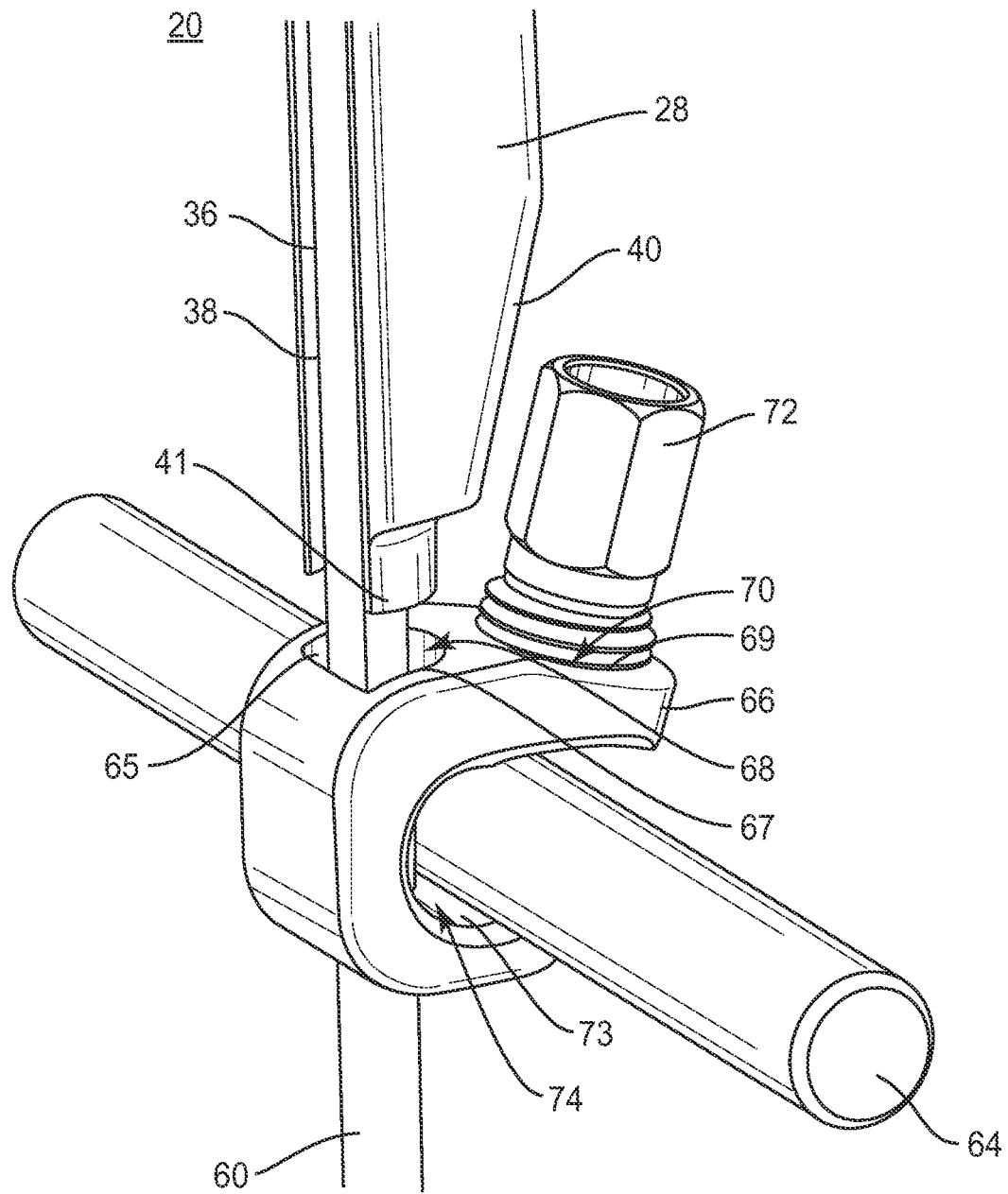
FIG. 5 is a break away perspective view of components of one embodiment of a spinal correction system in accordance with the present disclosure.
Figure 6:
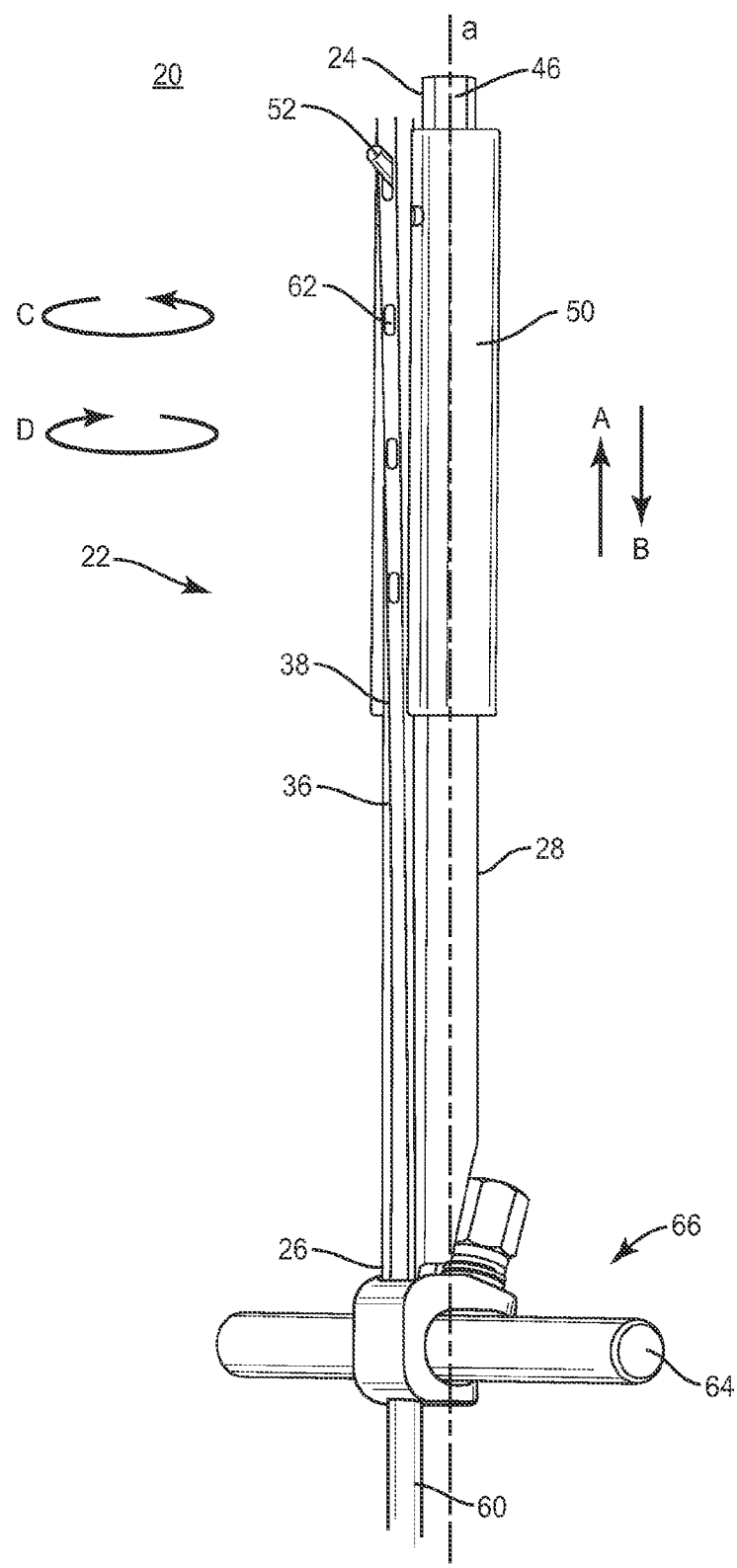
FIG. 6 is a perspective view of the system shown in FIG. 5.
Figure 7:
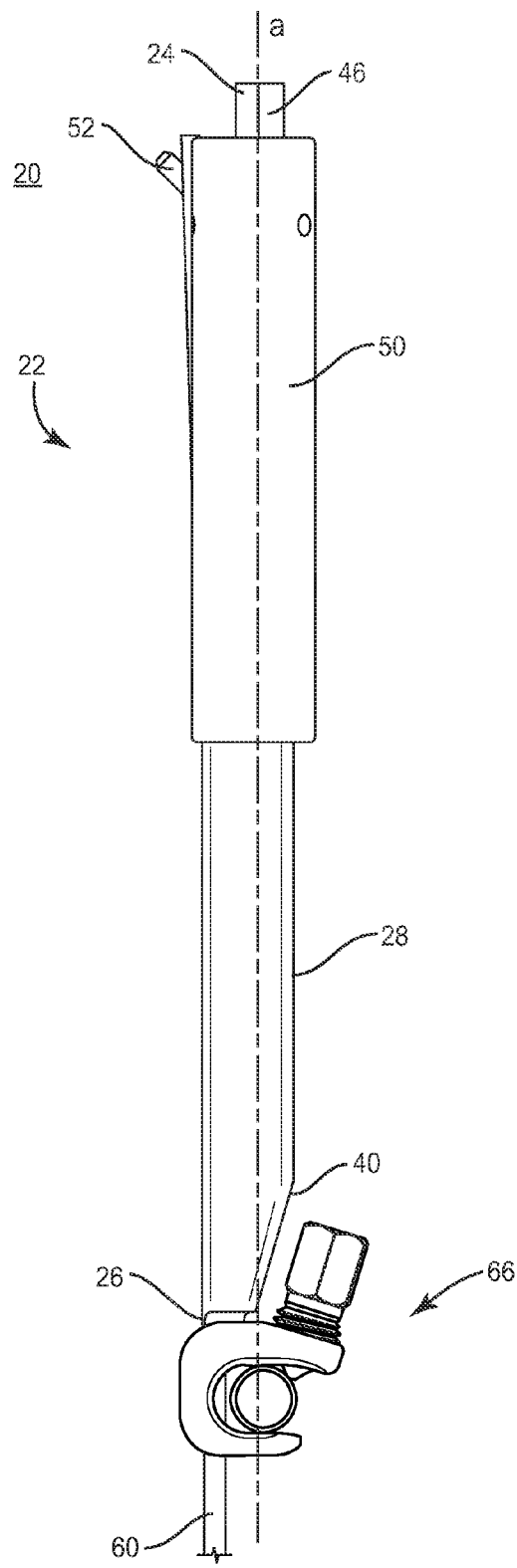
FIG. 7 is a side view of the system shown in FIG. 6.

In operation of instrument 22, implants 60, 64 are provisionally captured within passageways 68, 74 respectively of connector 66. Tip 41 engages recess 65 to dock connector 66 with instrument 22, as shown in FIG. 5. The proximal end of tether 60 is introduced into channel 36 via opening 38. Pin 52 is disposed with a selected opening 62 for engaging tether 60, as shown in FIGS. 5-6. The distal end of tether 60 is disposed via a loop about a selected vertebrae, as shown in FIG. 4. Screw 46 is rotatable within body 28 via threaded engagement of 48, 42. To apply tension to tether 60, screw 46 is rotated in the clockwise direction, as shown by arrow D in FIG. 6, such that body 28 expands axially and translates in a first direction as shown by arrow B, relative to handle 50. Screw 46 is fixed with handle 50 and freely rotatable relative thereto, such that handle 50 axially translates in the direction of arrow A, relative to body 28. Handle 50 translates relative to body 28 such that instrument 22 expands and pin 52 draws and/or pulls tether 60 to apply a tensioning force to tether 60. This configuration tensions the loop disposed about vertebrae and tensions the components of system 20 adjacent the vertebrae for fixation therewith.

To release tension from tether 60, screw 46 is rotated in a second direction, such as, for example, a counter clockwise direction, as shown by arrow C in FIG. 6, such that body 28 axially translates in a second direction, as shown by arrow A, relative to handle 50. Handle 50 axially translates in the direction shown by arrow B, relative to body 28. Handle 50 translates relative to body 28 such that instrument 22 contracts and pin 52 translates to release tension from tether 60.

In assembly, operation and use, a surgical system including spinal correction system 20, similar to that described above, is employed with a surgical procedure, such as, for example, a correction treatment to treat adolescent idiopathic scoliosis and/or Scheuermann's kyphosis of a spine. It is contemplated that one or all of the components of spinal correction system 20 can be delivered or implanted as a pre-assembled device or can be assembled in situ. Spinal correction system 20 may be completely or partially revised, removed or replaced.

For example, spinal correction system 20 can be employed with a surgical correction treatment of an applicable condition or injury of an affected section of a spinal column and adjacent areas within a body, such as, for example, at least a first vertebra V1, a second vertebra V2, a third vertebra V3 and a fourth vertebra V4 of vertebrae V. It is envisioned that spinal correction system 20 may be employed with one or a plurality of vertebrae.

In use, to treat a selected section of vertebrae V, a medical practitioner obtains access to a surgical site including vertebrae V in any appropriate manner, such as through incision and retraction of tissues. It is envisioned that spinal correction system 20 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 20. A preparation instrument (not shown) can be employed to prepare tissue surfaces of vertebrae V, as well as for aspiration and irrigation of a surgical region according to the requirements of a particular surgical application.

Figure 9:
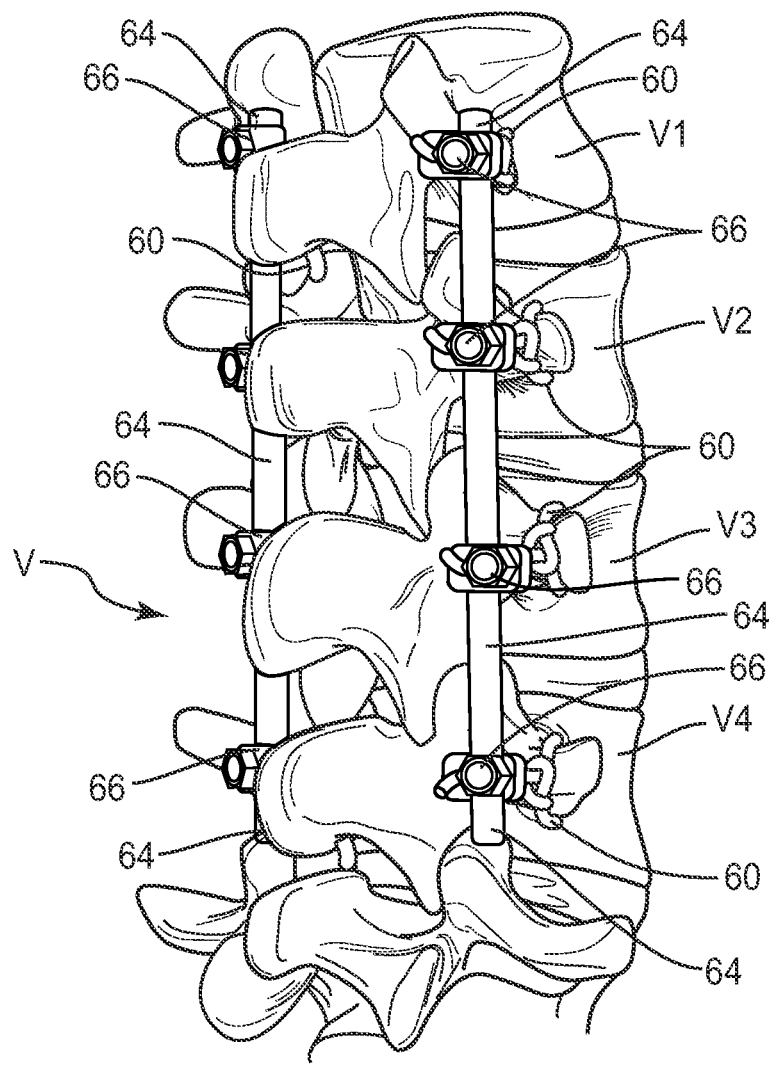
FIG. 9 is a perspective view of one embodiment of a spinal correction system in accordance with the principles of the present disclosure disposed with vertebrae.
Figure 10:
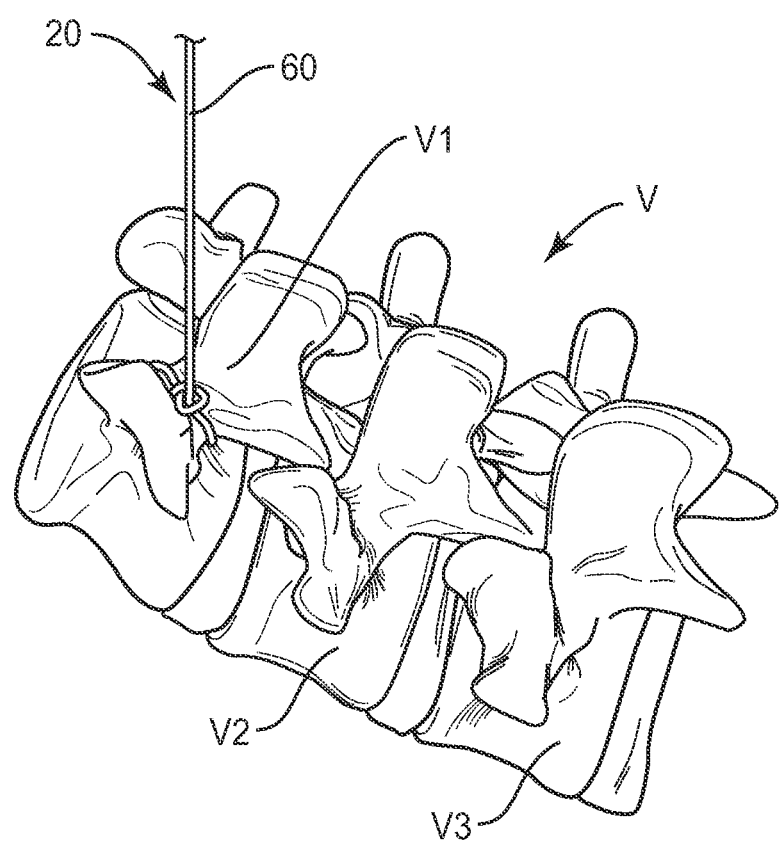
FIG. 10 is a perspective view of a component of the system shown in FIG. 1 disposed with vertebrae.
Figure 11:
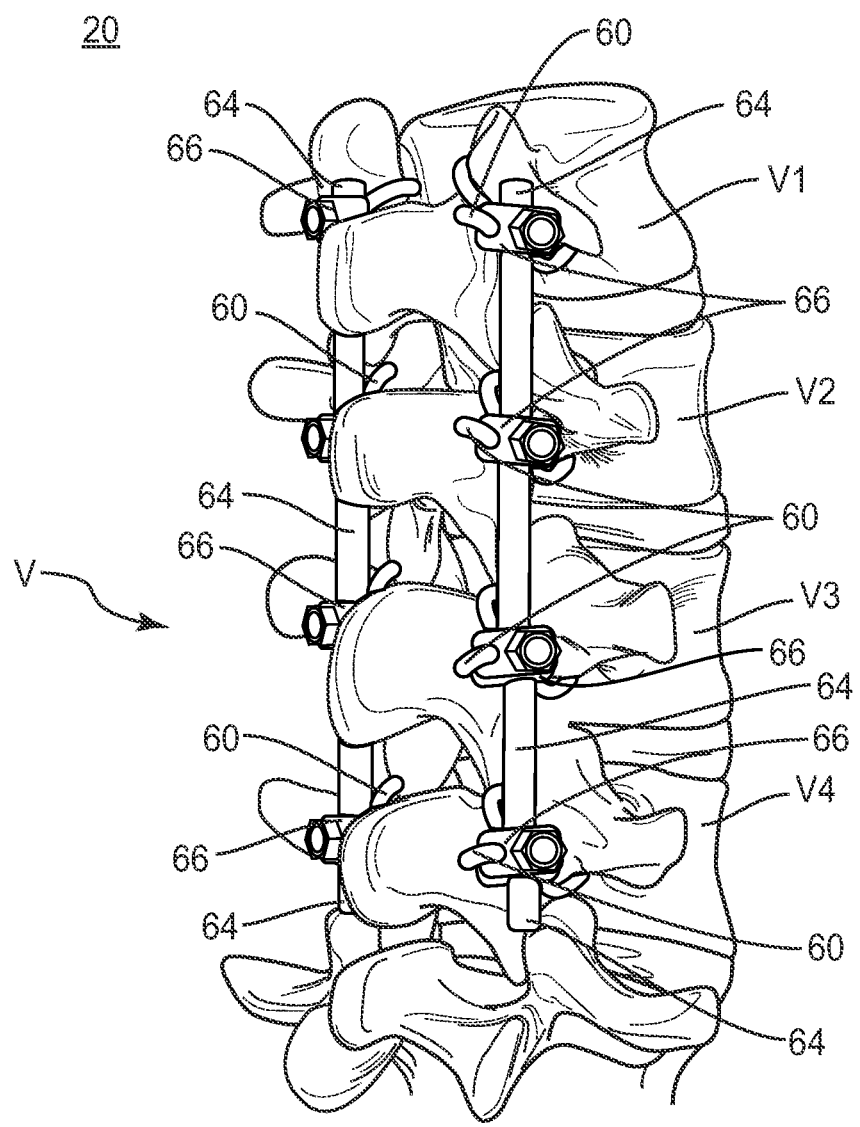
FIG. 11 is a perspective view of one embodiment of a spinal correction system in accordance with the principles of the present disclosure disposed with vertebrae.
Figure 12:
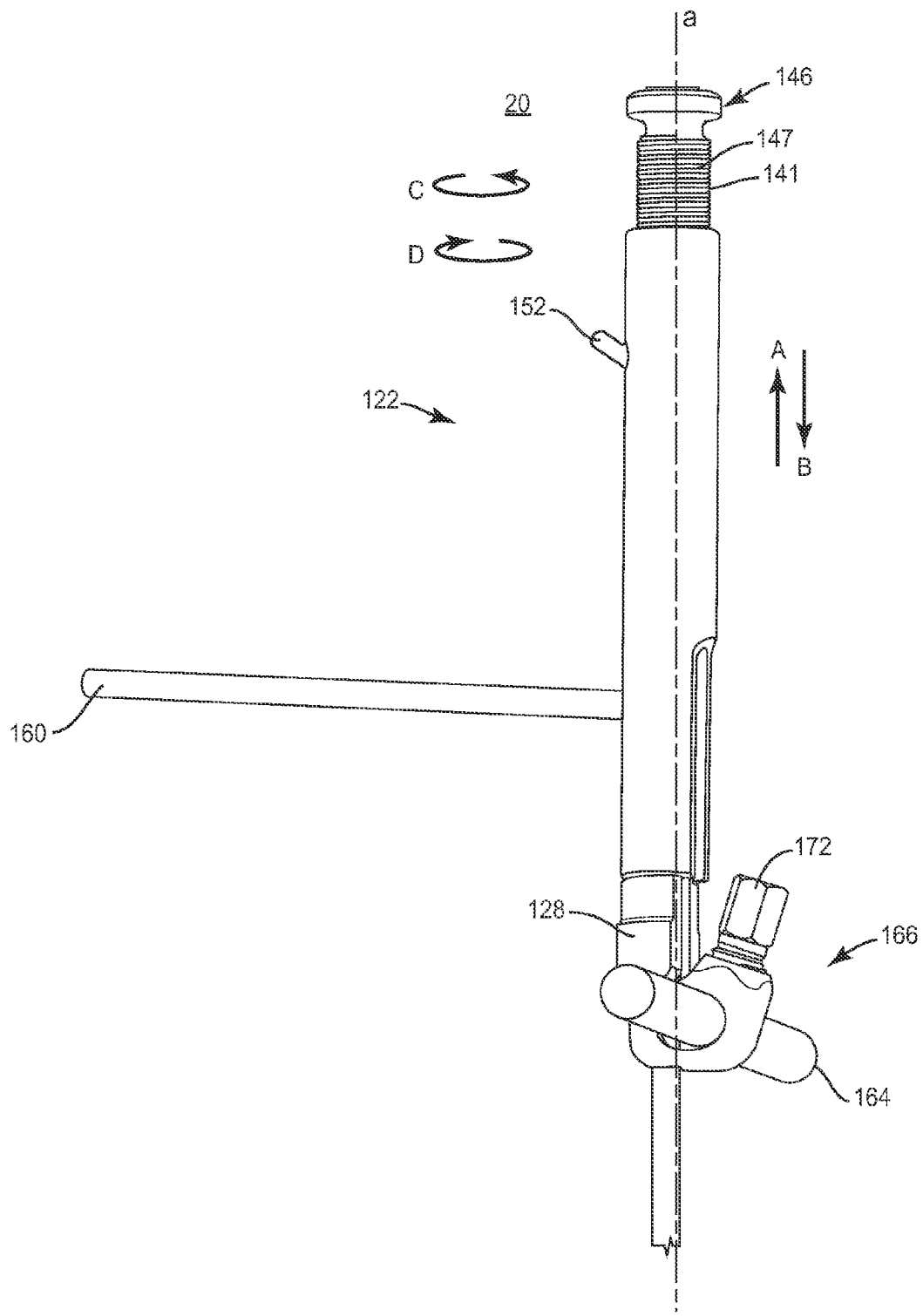
FIG. 12 is a perspective view of one embodiment of a spinal correction system in accordance with the principles of the present disclosure.
Figure 13:
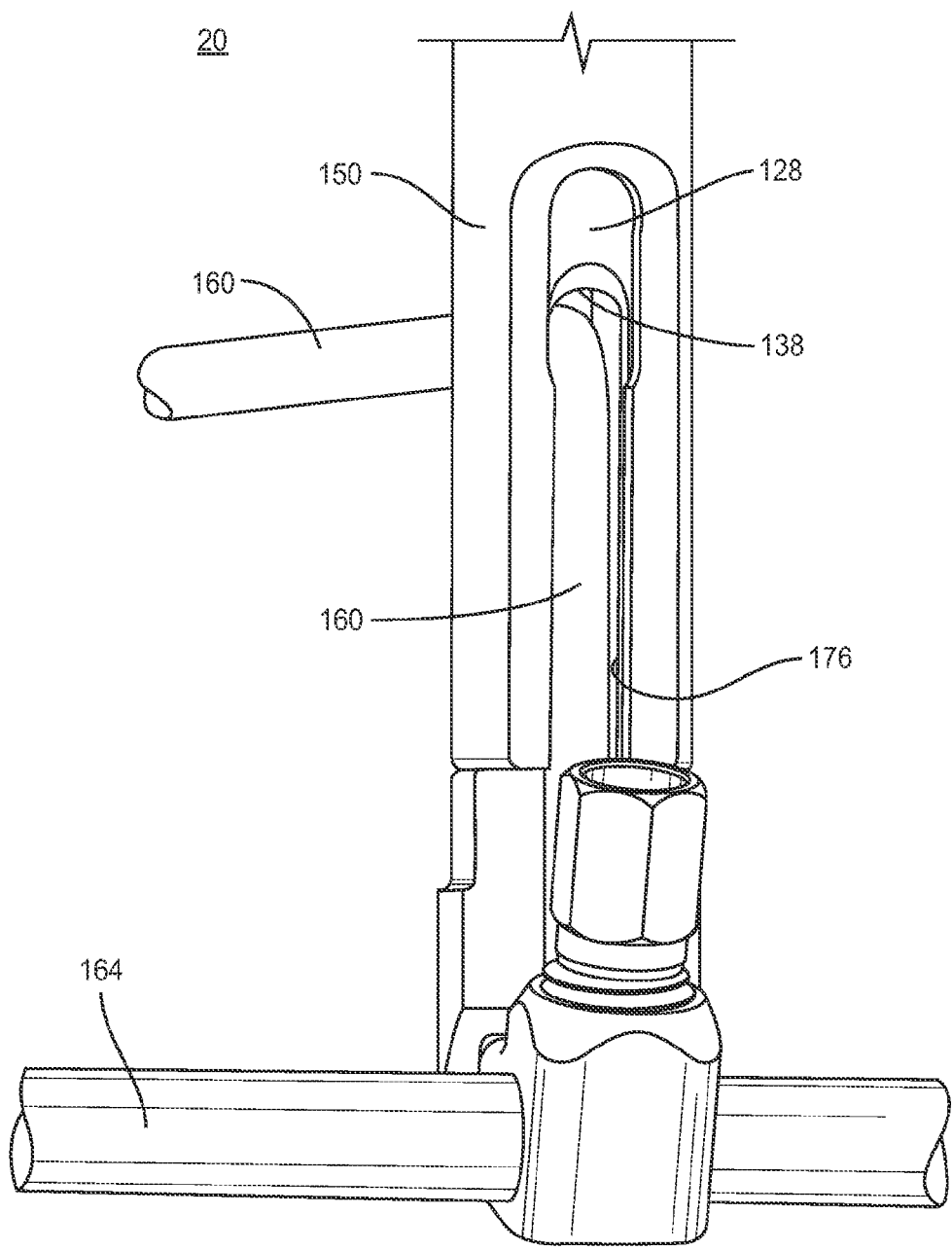
FIG. 13 is an enlarged perspective view of the system shown in FIG. 12.
Figure 14:
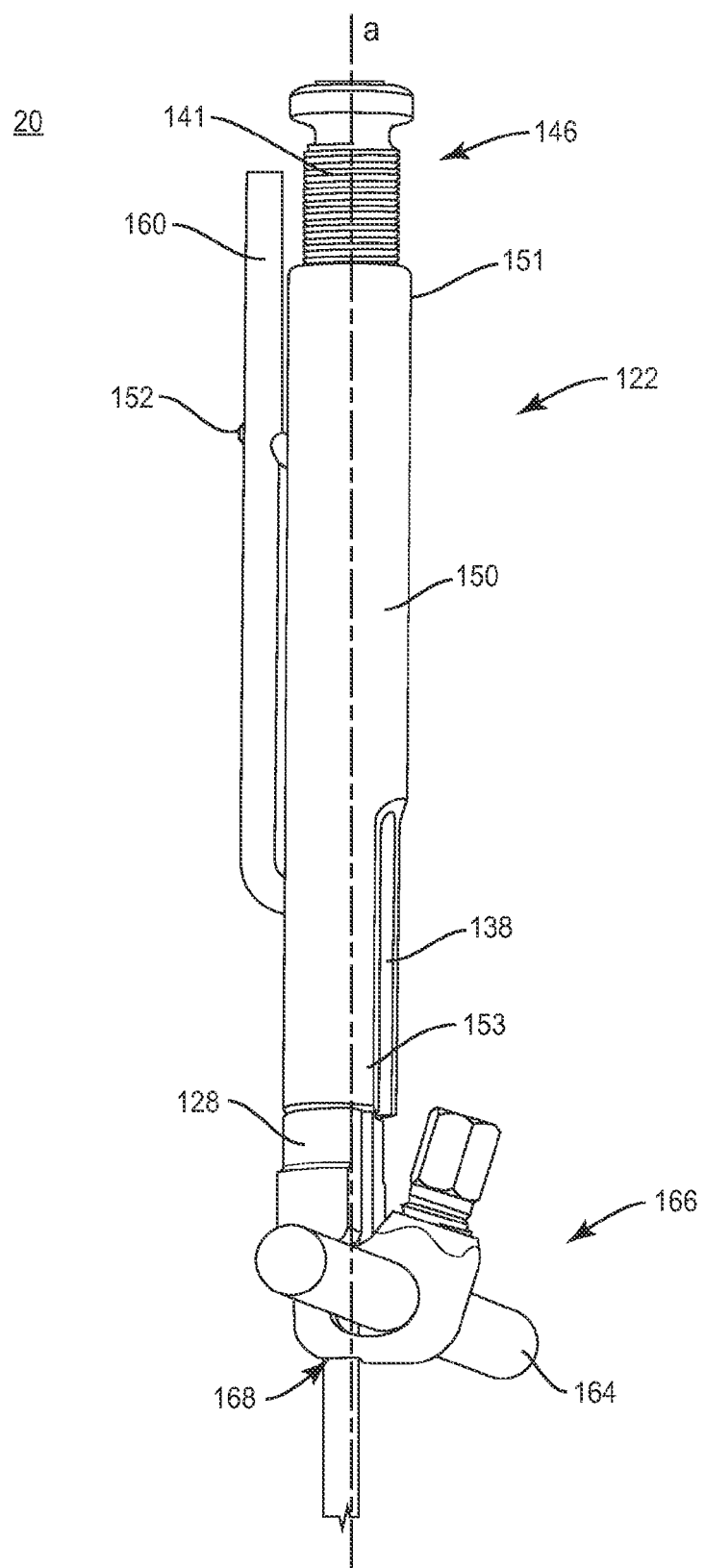
FIG. 14 is a perspective view of the system shown in FIG. 12.

Tether 60 is delivered along the surgical pathway to a surgical site adjacent vertebrae V. Tether 60 is disposed with vertebra V1. In one embodiment, as shown in FIGS. 4 and 9, a loop of tether 60 is disposed about a transverse process of vertebra V2 by passing the first end continuously about the transverse process. The second free end is passed through the loop cavity and drawn away from vertebra V2. The second free end is drawn and/or tensioned to tighten the first end with the outer surface of the transverse process in a loop knot. In one embodiment, as shown in FIGS. 10 and 11, a loop is disposed about a lamina of vertebra V1 by passing a first end continuously about the lamina. The second free end is passed through a loop cavity and drawn away from vertebra V1. The second free end is drawn and/or tensioned to tighten the first end with the outer surface of the lamina in a loop knot. This configuration fixes and/or attaches the first end of tether 60 with the transverse process and/or lamina.

Upon disposal of the first end of tether 60 with a vertebra, tether 60 is disposed with passageway 68 and rod 64 is disposed with passageway 74 of connector 66, as shown in FIGS. 5 and 6. Connector 66 is reduced adjacent the vertebrae. Tip 41 of instrument 22 is docked with recess 65, as described. Tether 60 is introduced into channel 36 of body 28 via opening 38. Pin 52 is disposed with a selected opening 62 for engaging tether 66 to handle 50.

Screw 46 is rotatable within body 28 via threaded engagement of 48, 42. To apply tension to tether 60, screw 46 is rotated in the clockwise direction, as shown by arrow D in FIG. 6, such that body 28 expands axially and translates in a first direction as shown by arrow B, relative to handle 50. Screw 46 is fixed with handle 50 and freely rotatable relative thereto, such that handle 50 axially translates in the direction of arrow A, relative to body 28. Handle 50 translates relative to body 28 such that instrument 22 expands and pin 52 draws and/or pulls tether 60 to apply a tensioning force to tether 60. This configuration tensions the loop disposed about vertebrae and tensions the components of system 20 adjacent the vertebrae for fixation therewith.

To release tension from tether 60, screw 46 is rotated in a second direction, such as, for example, a counter clockwise direction, as shown by arrow C in FIG. 6, such that body 28 axially translates in a second direction, as shown by arrow A, relative to handle 50. Handle 50 axially translates in the direction shown by arrow B, relative to body 28. Handle 50 translates relative to body 28 such that instrument 22 contracts and pin 52 translates to release tension from tether 60.

In one embodiment, spinal correction system 20 includes a second connector, similar to first connector 66 and spaced apart from first connector 66 along spinal rod 64. Second connector 66 is configured for disposal of a second flexible tether 60, separate from first flexible tether 60, which is tensioned with vertebra V1. Spinal correction system 20 includes a third connector and a fourth connector, similar to first connector 60, which are configured for disposal of tethers 60 tensioned with vertebra V3, V4, respectively. Spinal rod 64 is disposed with vertebrae V along a first side of the spinous process. Spinal correction system 20 includes a second spinal rod 64 mounted with a plurality of connectors 66 and tethers 60 along a second side of the spinous process. Spinal rods 64 are mounted with vertebrae V in a side by side orientation according to the requirements of a particular application. As such, spinal correction system 20 stabilizes vertebrae V and affects growth for a correction treatment to treat various spine pathologies.

Upon completion of the procedure, the surgical instruments and assemblies are removed and the incision is closed. Spinal correction system 20 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of spinal correction system 20.

It is contemplated that the components of spinal correction system 20 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. It is further contemplated that the components of spinal correction system 20 and related methods may be used to prevent or minimize curve progression in individuals of various ages.

In one embodiment, as shown in FIGS. 12-15, spinal correction system 20, similar to the apparatus and methods described above with regard to FIGS. 1-11, includes an implant instrument 122. Instrument 122 extends between a proximal end 124 and a distal end 126. Instrument 122 defines a longitudinal axis a that extends between ends 124, 126.

Instrument 122 includes a body 128 that extends between a proximal end 130 and a distal end 132. End 130 is configured for engagement with a lead screw and end 132 is configured to mate and/or dock with a connector, as described. Body 128 includes a first lateral opening 136 for disposal of a tether 160, similar to tether 60 described above, and a second lateral opening 138 configured for loading of tether 160 and providing clearance for a setscrew driver, as described. Opening 138 is configured to provide a window for tether loading. Opening 136 is configured to provide lateral passage of a tether through instrument 122. Tether 160 includes a plurality of spaced apart lateral openings 162 configured for engagement with a pin 152, similar to pin 52 described above, of a handle 150, described below. Pin 152 is angled upward to prevent tether 160 from disengaging from handle 150.

Figure 15:
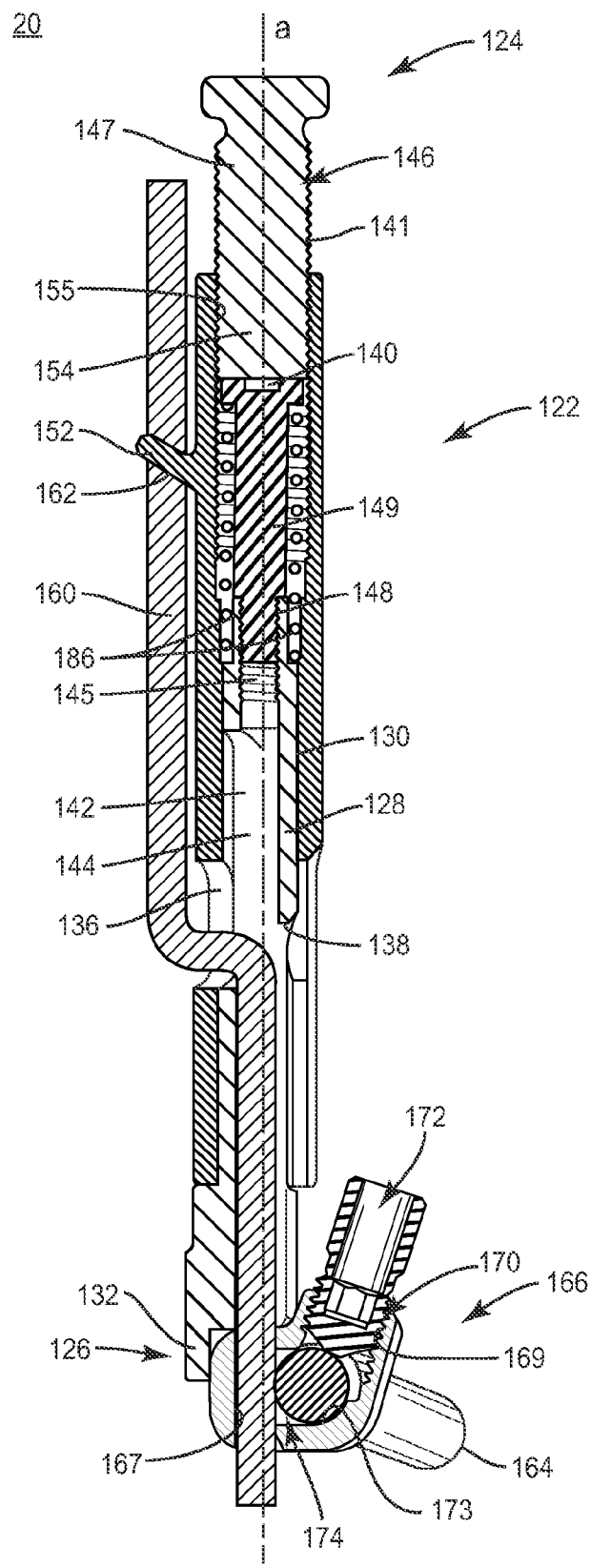
FIG. 15 is a cross-section view of the system shown in FIG. 14.

Body 128 includes an inner surface 142, as shown in FIG. 15. Surface 142 defines an axial cavity 144 that extends through at least a portion of body 128. Cavity 144 extends along longitudinal axis a. Cavity 144 is disposed in communication with openings 136, 138. Cavity 144 includes a threaded portion 145 configured for fixation with a screw, such as, for example, a lead screw 146.

Lead screw 146 includes a first member 147 and a second member 149 connected via a pin 140. Pin 140 fixes member 147 with member 149 such that member 147 is freely rotatable relative to member 149. Member 149 includes a threaded outer surface 148 that mates with portion 145 for fixation of screw 146 with body 128. Screw 146 mates with body 128 such that body 128 axially translates with screw 146. Member 147 includes an outer threaded surface 141.

A handle 150 extends between a proximal end 151 and a distal end 153. Handle 150 includes an inner threaded surface 155 that defines an axial cavity 154. Surface 141 mates with surface 155 to cause axial translation of handle 150 relative to screw 146. A spring 186 is disposed in cavity 154 and engages member 149 and body 128 to resiliently bias member 149 and body 128 apart along axis a, such as, for example, to a closed position such that body 128 translates axially in the direction shown by arrow B in FIG. 12 to close opening 138. This configuration prevents loading and/or interference with a loaded tether.

Spinal correction system 20 includes a spinal rod 164, similar to rod 64 described above. Spinal correction system 20 includes an implant connector 166, similar to connector 66 described above. The body of connector 166 includes an inner surface 167 that defines a passageway 168. Passageway 168 defines a first axis and is configured for disposal of tether 160. The body of connector 166 includes an inner surface 169 that defines a passageway 170. Inner surface 169 includes an internal thread form configured for engagement with a set screw 172. Passageway 170 defines a second axis disposed at an angular orientation. The body of connector 166 includes an inner surface 173 that defines a passageway 174. Passageway 174 has an oblong configuration and extends through the body. Passageway 174 defines a third axis disposed in a transverse orientation relative to the first and second axes of connector 166. Passageway 174 is configured for disposal of spinal rod 164 such that connector 166 can be mounted with spinal rod 164, according to the requirements of a particular application.

In operation of instrument 122, implants 160, 164 are provisionally captured within passageways 168, 174 respectively of connector 166. End 132 docks with connector 166. Tether 160 is introduced through openings 138, 136 and drawn in a lateral direction, transverse to axis a, relative to instrument 122. Tether 160 is manipulated and pin 152 is disposed with a selected opening 162 for engaging tether 160. The distal end of tether 160 is disposed via a loop about a selected vertebra, as described. Member 147 is rotatable within handle 150 via threaded engagement of surfaces 141, 155. To apply tension to tether 160, member 147 is rotated in a clockwise direction, as shown by arrow D in FIG. 12, such that screw 146 applies a force against spring 186 and engages body 128 to expand axially and translate in the direction shown by arrow B, relative to handle 150. Handle 150 axially translates in the direction shown by arrow A, relative to body 128. Handle 150 translates relative to body 128 such that instrument 122 expands and pin 152 draws and/or pulls tether 160 to apply a tensioning force to tether 160. This configuration tensions the loop disposed about vertebrae and tensions the components of system 20 adjacent the vertebrae for fixation therewith.

To release tension from tether 160, member 147 is rotated in a counter clockwise direction, as shown by arrow C, such that body 128 axially translates in the direction shown by arrow A, relative to handle 150. Handle 150 axially translates in the direction shown by arrow B, relative to body 128. Handle 150 translates relative to body 128 such that instrument 122 contracts and pin 152 translates to release tension from tether 160.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a first member having a first surface defining a first cavity for disposal of a first implant and a distal end configured to mate with a recess of a connector, the first member defining a second cavity;
a second member configured for movable disposal in the second cavity; and
a third member connected to the proximal end of the second member and the first implant,
wherein the second member is axially movable in a first direction to tension the first implant and in a second direction to release tension from the first implant,
wherein the third member includes a lateral projection and the first implant includes a plurality of spaced apart axial openings, the projection being disposable in the openings.

2. An instrument according to claim 1, wherein the connector includes an outer surface defining the recess and a first passageway configured for disposal of the first implant, the connector further including an inner surface that defines a second passageway configured for disposal of a second implant.

3. An instrument according to claim 2, wherein the first passageway is disposed in a transverse orientation relative to the second passageway.

4. An instrument according to claim 1, wherein the connector includes a coupling element configured to engage and fix the second implant with the connector.

5. An instrument according to claim 4, wherein the distal end includes an angled surface configured for providing clearance about the coupling element.

6. An instrument according to claim 1, wherein the distal end includes a reduced diameter portion configured for disposal in the recess.

7. An instrument according to claim 1, wherein the first cavity has a longitudinal orientation extending between a first end and a second end of the instrument.

8. An instrument according to claim 1, wherein the first cavity has a longitudinal orientation and the first surface has a concave configuration.

9. An instrument according to claim 1, wherein the first member defines at least one lateral opening that communicates with the first cavity.

10. An instrument according to claim 1, wherein the second member is configured for axial translation relative to the first member.

11. An instrument according to claim 1, wherein the first member includes a threaded inner surface and the second member includes a threaded outer surface, the surfaces being engageable to cause axial translation of the second member relative to the first member.

12. An instrument according to claim 1, wherein the second member is connected to the third member via a pinned interface.

13. An instrument according to claim 1, wherein the third member includes a lateral projection configured to engage and tension the first implant.

14. An instrument according to claim 1, wherein the first implant extends to a distal end, the distal end includes a loop configured for disposal about a transverse process of vertebrae.

15. An instrument according to claim 1, wherein the second member is fixed with and rotatable relative to the third member such that the second member is rotatable and engageable with the first member to cause axial translation of the first member and the third member relative to the second member.

16. A spinal implant system comprising:
a connector including an outer surface defining a recess and a first passageway and a second passageway disposed in a transverse orientation relative to the first passageway;
a tether being disposable in at least the first passageway and extending between a proximal end and a distal end, the tether comprising a plurality of spaced apart lateral openings disposed longitudinally therealong, the distal end of the tether including a loop configured for disposal about vertebrae;
a spinal rod being disposable in at least the second passageway and extending between a first end and a second end; and
an instrument defining a longitudinal axis and including a body extending between a proximal end and a distal end, the body including an outer surface having a concave portion defining an axial channel configured for disposal of the tether, the outer surface of the body defining a lateral opening disposed in communication with the axial channel, the distal end of the body including an angled surface and a reduced diameter portion configured to mate with the recess, the body further including an inner threaded surface that defines a translation cavity,
the instrument further including a lead screw including a threaded outer surface engageable with the inner threaded surface, and
the instrument further including a handle fixed with the lead screw via a pinned interface such that the lead screw is relatively rotatable therefrom, the handle including a lateral projection configured for disposal in the lateral openings, the handle defining a lateral opening disposed in communication with the axial channel,
wherein the lead screw is rotatable in a clockwise direction to cause axial translation of the body relative to the lead screw in a first direction such that the projection tensions the tether and the lead screw is rotatable in a counter clockwise direction to cause axial translation of the body relative to the lead screw in a second direction to release tension from the tether.

17. A method for treating a spine disorder, the method comprising the steps of:
providing a first flexible implant; disposing the first flexible implant with a first vertebra;
providing a first connector including an outer surface defining a recess and an inner surface defining a first passageway and a second passageway;
disposing the first flexible implant in the first passageway;
providing a second implant; disposing the second implant in the second passageway;
providing an instrument comprising:
a first member having a first surface defining a first cavity and a distal end, the first member defining a second cavity,
a second member configured for movable disposal in the second cavity, and
a third member connected to the proximal end of the second member;
disposing the first flexible implant in the first cavity;
mating the distal end with the recess;
delivering the connector to adjacent the first vertebra with the instrument; connecting the first flexible implant with the third member; and
axially translating the first member relative to the second member in a first direction such that the third member tensions the first flexible implant and in a second direction such that the third member releases tension from the first flexible implant.

18. A method according to claim 17, wherein the step of disposing the first flexible implant includes passing the first flexible implant through a lateral opening of the first member into the first cavity.

19. A method according to claim 17, wherein the step of axially translating includes rotating the second member to cause axial translation of the first member relative to the second member.

* * * * *